United States Patent [19]

Terrell

[11] Patent Number: 4,762,856
[45] Date of Patent: Aug. 9, 1988

[54] ANESTHETIC COMPOSITION AND METHOD OF USING THE SAME

[75] Inventor: Ross C. Terrell, Clark, N.J.

[73] Assignee: BOC, Inc., Montvale, N.J.

[21] Appl. No.: 10,106

[22] Filed: Feb. 2, 1987

[51] Int. Cl.$^4$ .............................................. A61K 31/08
[52] U.S. Cl. .................................................. 514/722
[58] Field of Search ........................................ 514/722

[56] References Cited

U.S. PATENT DOCUMENTS

| | | | |
|---|---|---|---|
| 3,535,425 | 10/1970 | Terrell et al. | 514/722 |
| 3,609,196 | 9/1971 | Terrell | 514/722 |
| 3,764,705 | 10/1973 | Terrell | 514/722 |
| 3,897,502 | 7/1975 | Russell et al. | 549/455 |
| 3,980,714 | 9/1976 | Siegemund | 514/722 |
| 4,113,883 | 9/1978 | Bagnall | 514/722 |
| 4,559,154 | 12/1985 | Powell | 252/69 |

OTHER PUBLICATIONS

Bart, A. J. et al. "Changes in Power of Electroencephalograms During Anesthesia with Fluroxene, Methoxyflurane and Ethrane38 (Feb. 1971), 11 pages.

Koblin, D. D. et al. "Minimum Alveolar Concentrations and Oil/Gas Partition Coefficients of Four Anestheitc Isomers" (Apr. 1981), 4 pages.

R. Terrell, "Halogenated Methyl Ethyl Ethers as Anesthetic Agents" Oct. 10, 1970 (pp. 517–519) J. Med. Chem., 14(6) (Jun. 1971).

R. Terrell, "Fluorinated Methyl Ethyl Ethers as Anesthetic Agents" Dec. 6, 1971 (pp. 604–606) J. Med. Chem., 15(6) (Jun. 1972).

P. E. Aldrich and William A. Sheppard, "Fluorinated Ethers, II. Alkyl Fluoroalkyl Ethers[1]" Jul. 1, 1963 (pp. 11–15) J. Org. Chem., 29(14) (Jan. 1964).

K. K. Johri and D. D. DesMarteau, "Comparison of the Reactivity of $CF_3OX(X=Cl,F)$ with some Simple Alkenes", Jul. 26, 1982 (pp. 242–250) J. Org. Chem., 48(2) 1983.

Primary Examiner—Jerome D. Goldberg
Attorney, Agent, or Firm—Chris P. Konkol; Larry R. Cassett

[57] ABSTRACT

The present invention is directed to an anesthesia inducing composition comprising a mixture of oxygen gas and an anesthesia inducing effective amount of a compound 2-(difluoromethoxy)-1,1,1,2-tetrafluoroethane having the formula

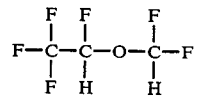

The present invention is also directed to methods of inducing and/or maintaining anesthesia by administering the composition in sufficient amounts to warm blooded animals.

1 Claim, No Drawings

ANESTHETIC COMPOSITION AND METHOD OF USING THE SAME

FIELD OF THE INVENTION

The present invention is directed to the field of inhalation anesthetics and particularly to volatile liquid inhalation anesthetics which are used to induce and maintain anesthesia.

BACKGROUND OF THE INVENTION

Volatile liquid anesthetics are known in the art and include by way of example halothane, trichloroethylene and ether derivatives including enflurane, fluroxene, methoxyflurane, and isoflurane.

The aforementioned inhalation anesthetics overcome many of the limitations inherent in earlier agents such as chloroform and ether. These anesthetics act rapidly, have minimal or no toxicity, and are non-flammable. Despite this considerable progress, one limitation continues to be the rate at which recovery from anesthesia occurs. Although recovery is rapid, it is less rapid than might be desired, especially for patients who return home on the day of surgery (outpatient surgery).

The compound employed in the composition of the present invention, 2-(difluoromethoxy)-1,1,1,2-tetrafluoroethane or $CHF_2OCHFCF_3$, is disclosed in Example XXI of Russell et al., U.S. Pat. No. 3,897,502, which is directed to processes for making fluorinated ethers to prepare pastes and dispersions of fluorine-containing olefins, waxes to provide coatings, and degreasing agents. Furthermore, the Russel et al. patent states that some of the poly-fluoro containing products which can be made by the methods disclosed in the patent are agents for producing anesthesia in anesthetic-susceptible, air-breathing mammals.

Applicants have found that the compound of the present invention is an effective anesthetic and exhibits unexpectedly rapid induction and recovery.

It is therefore an object of the invention to provide an anesthetic composition which exhibits rapid induction and recovery times.

It is a further object of the invention to provide an anesthetic composition that is resistant to breakdown, exhibits little or no toxicity and is relatively safe to use.

It is still a further object of the invention to provide methods of inducing anesthesia employing an anesthetic composition that is fast acting and affords the patient rapid recovery from anesthesia.

DETAILED DESCRIPTION OF THE INVENTION

The present invention is directed to an anesthesia inducing composition comprising a mixture of oxygen gas and an anesthesia inducing effective amount of a compound 2-(difluoromethoxy)-1,1,1,2-tetrafluoroethane having the formula

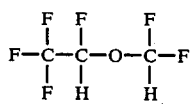

The present invention is also directed to methods of inducing and/or maintaining anesthesia by administering the composition in sufficient amounts to warm blooded animals.

The compound of the present invention lends itself to effective use as an inhalant anesthetic in respirable mixtures containing life-supporting concentrations of oxygen, with or without other inhalation anesthetics, such as nitrous oxide. Administration of the compound may be by any of the well known techniques for administering general inhalation anesthetics, for example, by using the open drop or semi-closed systems.

The effective amount of the compounds of this invention to be employed depends on the level of anesthesia to which the mammal is to be brought, the rate at which anesthesia is to be induced, and the length of time over which anesthesia is to be maintained. Minor volume percentages of the compound in oxygen can often be employed. The amount used should be sufficient to provide a significant anesthetic effect but not so much as to produce unacceptable deleterious side effects. For instance, about 1 to 8 volume percent of the compound may often be used. About 3 to 7 volume percent is preferred. The amount of anesthesia to be used can be regulated, starting with a small amount of the compound and gradually increasing the amount until the desired plane of anesthesia is reached. By then monitoring the physical reactions of the mammal, as is the usual procedure, the duration and plane of anesthesia can be readily controlled.

The compound 2-(difluoromethoxy)-1,1,1,2-tetrafluoroethane is normally a clear, colorless liquid with a slight non-pungent odor. It has the following physical properties: boiling point 23.5° C., molecular weight 168, vapor pressure (est.) 660 mm Hg at 20° C., and specific gravity 1.44. The IR shows a prominent peak at 4903 and the $^1H$ NMR shows a triplet at 6.5 ppm (J=70 Hz) and a doublet of quartets at 5.9 ppm ($J_{gem}$=56 Hz, $J_{vic}$=3 Hz). The compound is non-flammable, and soda lime stable.

The compound $CHF_2OCHFCF_3$ can be prepared by the method described in U.S. Pat. No. 3,987,502 which is incorporated herein by reference. More specifically, a compound having the formula $CHF_2OCH_2CF_3$ is combined with freon and reacted with a mixture of 20% fluorine in argon followed by distillation.

In accordance with the present invention, the compound may also be prepared by reacting isoflurane ($CHF_2OCHClCF_3$) with a fluorine containing compound such as bromine trifluoride or with potassium fluoride.

Isoflurane used as a starting material for the above synthesis may be prepared by the methods disclosed in Terrell et al., U.S. Pat. No. 3,535,388, incorporated herein by reference.

The composition of the present invention includes a gaseous mixture of oxygen and the compound $CHF_2OCHFCF_3$.

EXAMPLE 1

PREPARATION OF $CHF_2OCHFCF_3$ 12.9 g of isoflurane (FORANE ® isoflurane commercially available from Anaquest Division of BOC, Inc. in Madison, Wis.) were combined with 5.5 g of potassium fluoride and 20 ml of diethylglycol and the mixture was heated with stirring for 10 hours in a glass pressure vessel at 195° C. The heated mixture was washed with ice water and the organic layer was subjected to gas chromatography, which showed the presence of the compound $CHF_2OCHFCF_3$ (29% yield).

EXAMPLE 2

PREPARATION OF CHF$_2$OCHFCF$_3$ 171 g of isoflurane were combined with 116 g of potassium fluoride in the absence of solvent and the resulting mixture was heated in an autoclave at 28° C. at 500 psi for 18 hours and then allowed to cool. The cooled mixture was subjected to gas chromatography which showed the presence of 68% of the compound CHF$_2$OCHFCF$_3$ and 30% unreacted isoflurane. Treatment of this mixture with excess bromine trifluoride at 15° C. in a glass vessel followed by washing with dilute sodium hydroxide and drying yielded 50 g of 98% pure product (30% yield).

EXAMPLE 3

PREPARATION OF CHF$_2$OCHFCF$_3$ 15.5 g of isoflurane was loaded into a 3-neck flask reactor equipped with a thermometer and stir bar. 2 ml of BrF$_3$ was added over 2½ hours while maintaining the temperature at about 14°–18° C. The reaction product was then allowed to stand overnight at ambient temperature. The reaction product was treated with 5% sodium hydroxide and the resulting organic layer was separated (9.0 g) and then subjected to gas chromatography to obtain 8.0 g of the compound CHF$_2$OCHFCF$_3$ (62% yield).

EXAMPLE 4

DETERMINATION OF SOLUBILITY OF CHF$_2$OCHFCF$_3$

Determination of the blood/gas and saline/gas partition coefficients of CHF$_2$CHFCF$_3$ was obtained using the method of Lerman et al. ("Age and Solubility of Volatile Anesthetic in Blood", Anesthesiology 61: 139–43, 1984). A 30 ml sample of venous blood was obtained from each of 11 ASA physical status I–III patients (4 female and 7 males) ranging in age from 25 to 76 years. Each sample was divided in half. Each 15 ml sample of blood or 0.9% saline was placed in a 50 ml syringe and equilibrated by tonometry with 20 ml of 1.6–2.6% of the compound CHF$_2$OCHFCF$_3$ for 90 min. in a waterbath at 37° C. The syringes were shaken vigorously every 15 minutes. The concentration of the compound in the gas phase over each sample was determined by gas chromatography using a 30 meter long, fused silica open tubular capillary (0.53 mm internal diameter) column coated with a 1.5 micron thick layer of methylsilicone oil (J&W Scientifice DB-1). A nitrogen carrier stream of 6 ml/min was directed through the column with a "make-up" flow of nitrogen of 40 ml/min delivered to the detector. A flame ionization detector at 200° C. was supplied by hydrogen at 40 ml/min and by air at 280 ml/min. Samples were injected with a 0.05 ml gas sample loop.

An aliquot of 10.069 ml of the equilibrated blood or saline was transferred anaerobically to a 581 ml flask from which a portion of the air had been evacuated to produce a negative pressure to draw the aliquot of blood or saline into the flask. Each flask was placed in a 37° C. water bath and shaken every 15 minuted for the ensuing 90 minutes. When this procedure was completed, the compound concentration in the gas phase of the flask was determined by gas chromatography. The blood/gas partition coefficient (lambda) was determined using the following equation:

$$\text{lambda} = \frac{C_s(V_f/V_s)}{C_f - C_s}$$

where $C_s$ is the concentration of the compound in the gas phase in the 30 ml syringe used for tonometry; $C_f$ is the concentration of the compound in the gas phase of the flask; $V_f$ is the volume of the flask; and $V_s$ is the volume of the aliquot of blood or saline.

Dual determinations of the partition coefficient were obtained for each patient. The paired values were averaged for each patient and the averaged value assumed to represent the partition coefficient for that patient's blood.

The blood/gas partition coefficient equaled 0.424±0.024. The saline/gas partition coefficient averaged 0.225±0.002.

Determinations of the oil/gas partition coefficient for the compound were obtained using the method described by Y. Tanifuji, "Some Characteristics of an Exceptionally Potent Inhaled Anesthetic: thiomethoxyflurane", Anesth. Analg. 56: 387–390, 1977. Liquid CHF$_2$OCHFCF$_3$ (0.15 ml) was added to 100 ml of pure virgin olive oil and thoroughly mixed. 12 ml of this mixture was equilibrated by tonometry with 20 ml of air for 15 hours in a 50 ml syringe placed in a 37° C. waterbath. The gas and oil were shaken vigorously once an hour for the last four hours of tonometry. The concentration of the compound in the gas phase over the olive oil was then determined by gas chomatography. An aliquot (10.069 ml) of the equilibrated mixture was placed in a 581 ml flask and the flask sealed with a Teflon stopper pierced with a needle to which was affixed a one-way stopcock. The flask was placed in a waterbath at 37° C. The flask was shaken vigorously once an hour for six hours. After six hours, the concentration of the compound in the gas above the mixture in the flask was determined by gas chromatography. The same general equation used above to calculate the blood/gas partition coefficient was used to calculate the oil/gas partition coefficient.

The oil/gas partition coefficient was 18.7±1.1.

EXAMPLE 5

TEST FOR ANESTHETIC PROPERTIES

Eight specific-pathogen-free, 2.5 month-old, male Sprague-Dawley rats weighing 381±18 g were housed individually in Plexiglass cylinders (chamber) having an internal diameter of 6.25 cm and a length of 29 cm. This diameter permitted the rat to crawl into the chamber, but prevented the rat from turning around.

The ends of the chamber were sealed with rubber stoppers. The stopper at the "head" end of the chamber was traversed by three catheters: one for sampling: one for injection of the compound CHF$_2$OCHFCF$_3$; and one for the delivery of oxygen. Oxygen was applied to the chamber at a bypass flow through rate of 500–600 ml per minute. The head end of the chamber also contained a carbon dioxide adsorber, charged with 50 g to 55 g of fresh, commercial (Sodasorb) soda lime.

The stopper at the "tail" end of the chamber was traversed by a catheter, a hole for the tail, and a hole through which a small rectal temperature probe was passed. The catheter was used to flush oxygen through the tube prior to initiation of injection of the anesthetic composition and to draw off gas when oxygen was introduced to lower the concentration of the compound.

A rectal probe was placed and secured in each of the rats. The tail was led out through the hole in the stopper and sealed. After placement of the rat in the chamber, a 3-3.4 l/min. flow of oxygen was directed through the chamber for 15 minutes. The chamber then was sealed except for the opening at the head end of the chamber to the oxygen bypass.

A gaseous mixture of the composition was produced by adding 0.2-0.25 ml of the liquid compound $CHF_2OCHFCF_3$ to 20 ml of oxygen in a 100 ml glass syringe sealed with a stopcock. This mixture was used to deliver the compound to the chamber. Anesthesia was rapidly induced by injection of a total of 50-75 ml of this mixture.

Injection of the mixture of the compound and oxygen rapidly produced anesthesia. In general, the recovery was comparatively rapid. Each animal began to move within one to two minutes following evacuation of the chamber. All survived and appears to be well 24 hours after anesthesia.

While there has been described what are at present considered to be preferred embodiments of the invention, it will be understood that various modifications may be made therein which are within the true spirit and scope of the invention.

I claim:

1. A method of inducing anesthesia in a warm blooded animal comprising administering by inhalation to said warm blooded animal an anesthesia inducing effective amount of 2-(difluoromethoxy)-1,1,1,2-tetrafluoroethane as an inhalation anesthetic while administering a life supporting amount of oxygen.

* * * * *

UNITED STATES PATENT AND TRADEMARK OFFICE

CERTIFICATE EXTENDING PATENT TERM
UNDER 35 U.S.C. § 156

PATENT NO.: 4,762,856

DATED: August 9, 1988

INVENTOR(S): Ross C. Terrell

PATENT OWNER: Anaquest, Inc.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

405 DAYS with all rights pertaining thereto as provided by 35 U.S.C. § 156(b).

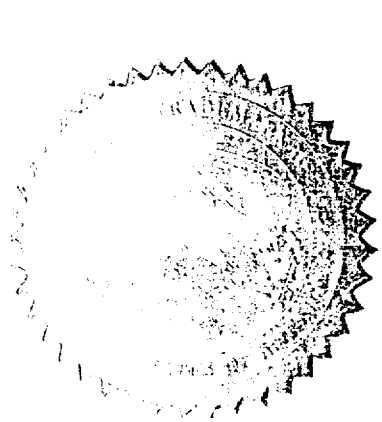

I have caused the seal of the Patent and Trademark Office to be affixed this 6th day of December 1993.

Bruce A. Lehman
Assistant Secretary of Commerce and
   Commissioner of Patents and Trademarks